US011000227B2

(12) United States Patent
Chuang et al.

(10) Patent No.: US 11,000,227 B2
(45) Date of Patent: May 11, 2021

(54) MEASUREMENT DEVICE AND METHOD FOR MEASURING PSYCHOLOGY STRESS INDEX AND BLOOD PRESSURE

(71) Applicant: AVITA CORPORATION, New Taipei (TW)

(72) Inventors: Li Heng Chuang, New Taipei (TW); I Chih Huang, New Taipei (TW)

(73) Assignee: AVITA CORPORATION, New Taipei (TW)

( * ) Notice: Subject to any disclaimer, the term of this patent is extended or adjusted under 35 U.S.C. 154(b) by 922 days.

(21) Appl. No.: 15/473,596

(22) Filed: Mar. 29, 2017

(65) Prior Publication Data

US 2017/0281080 A1 Oct. 5, 2017

(30) Foreign Application Priority Data

Mar. 29, 2016 (TW) .................. 105109918

(51) Int. Cl.
| | | |
|---|---|---|
| A61B 5/00 | (2006.01) | |
| A61B 5/024 | (2006.01) | |
| A61B 5/021 | (2006.01) | |
| A61B 5/022 | (2006.01) | |
| A61B 5/0205 | (2006.01) | |
| A61B 5/24 | (2021.01) | |
| A61B 5/0245 | (2006.01) | |
| A61B 5/16 | (2006.01) | |

(52) U.S. Cl.
CPC ............ *A61B 5/4884* (2013.01); *A61B 5/022* (2013.01); *A61B 5/0245* (2013.01); *A61B 5/02108* (2013.01); *A61B 5/02141* (2013.01); *A61B 5/02405* (2013.01); *A61B 5/24* (2021.01); *A61B 5/7253* (2013.01); *A61B 5/0205* (2013.01); *A61B 5/02116* (2013.01); *A61B 5/165* (2013.01)

(58) Field of Classification Search
CPC ..... A61B 5/022; A61B 5/024; A61B 5/02405; A61B 5/02444; A61B 5/025
See application file for complete search history.

(56) References Cited

U.S. PATENT DOCUMENTS

| 4,517,986 A | 5/1985 | Bilgutay | |
|---|---|---|---|
| 5,099,853 A * | 3/1992 | Uemura | ............. A61B 5/02116 600/492 |
| 6,171,254 B1 * | 1/2001 | Skelton | ................... A61B 5/022 600/485 |

(Continued)

FOREIGN PATENT DOCUMENTS

CN 101321490 12/2008

*Primary Examiner* — John R Downey
(74) *Attorney, Agent, or Firm* — Raymond Y. Chan; David and Raymond Patent Firm (57) ABSTRACT

A measurement device and method for measuring psychology stress index and blood pressure is disclosed. When the measurement device is in the psychology stress measurement mode and a pressurizing motor unit is pressurizing an airbag unit with a variable speed, the micro-processor unit may control the pressurizing motor unit to stop pressurizing the airbag unit after the pressure signal is determined as a pulse signal, and the micro-processor unit may measure the pulse signal to determine the psychology stress index. The psychology stress index is a ratio of SDNN and RMSSD according to interval data of the pulse signal within a period of time.

9 Claims, 6 Drawing Sheets

(56) References Cited

U.S. PATENT DOCUMENTS

| | | | |
|---|---|---|---|
| 7,217,237 B2 * | 5/2007 | Wassermann | A61F 2/004 600/29 |
| 2001/0012916 A1 * | 8/2001 | Deuter | A61B 5/02125 600/485 |
| 2002/0077558 A1 * | 6/2002 | Itonaga | A61B 5/02233 600/490 |
| 2004/0158162 A1 * | 8/2004 | Narimatsu | A61B 5/022 600/494 |
| 2004/0181157 A1 * | 9/2004 | Medero | A61B 5/02225 600/500 |
| 2005/0187480 A1 * | 8/2005 | Kario | A61B 5/022 600/483 |
| 2006/0173363 A1 * | 8/2006 | Felder | A61B 5/6843 600/485 |
| 2006/0229517 A1 * | 10/2006 | Lin | A61B 5/025 600/490 |
| 2008/0045846 A1 * | 2/2008 | Friedman | A61B 5/02225 600/490 |
| 2008/0294021 A1 * | 11/2008 | Lin | A61B 5/022 600/301 |
| 2009/0137912 A1 * | 5/2009 | Hirabara | A61B 5/022 600/485 |
| 2009/0234199 A1 * | 9/2009 | Takahashi | A61B 5/4812 600/301 |
| 2010/0210956 A1 * | 8/2010 | Im | A61B 5/02007 600/490 |
| 2011/0152650 A1 * | 6/2011 | Donehoo | A61B 5/02255 600/324 |
| 2012/0253209 A1 * | 10/2012 | Ukawa | A61B 5/02133 600/494 |
| 2013/0226012 A1 * | 8/2013 | Kinoshita | A61B 5/02108 600/490 |
| 2014/0163402 A1 * | 6/2014 | Lamego | A61B 5/0235 600/493 |
| 2014/0206944 A1 * | 7/2014 | Jain | A61B 5/0205 600/301 |
| 2014/0296734 A1 * | 10/2014 | Tu | A61B 5/6831 600/547 |
| 2014/0375785 A1 * | 12/2014 | Kogut | A61B 5/0205 348/77 |
| 2015/0038858 A1 * | 2/2015 | Ariga | A61B 5/0225 600/490 |
| 2015/0190064 A1 * | 7/2015 | Kinoshita | A61B 5/024 600/490 |
| 2015/0190093 A1 * | 7/2015 | Chang | A61B 5/6898 600/301 |
| 2015/0201847 A1 * | 7/2015 | Ono | A61B 5/022 600/490 |
| 2015/0245772 A1 * | 9/2015 | Kawamoto | A61B 5/7221 600/494 |
| 2015/0305634 A1 * | 10/2015 | Stergiou | A61B 5/02405 600/509 |
| 2016/0100765 A1 * | 4/2016 | Muehlsteff | A61B 5/022 600/490 |
| 2016/0120445 A1 * | 5/2016 | Peluso | A61B 5/1112 600/301 |
| 2016/0198967 A1 * | 7/2016 | Hsu | A61B 5/4854 600/501 |
| 2016/0213332 A1 * | 7/2016 | Ukawa | A61B 5/7278 |

* cited by examiner

MEASUREMENT DEVICE AND METHOD FOR MEASURING PSYCHOLOGY STRESS INDEX AND BLOOD PRESSURE

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a measurement device and method, and more particularly to a measurement device and method for measuring psychology stress index and blood pressure.

Description of Related Arts

The modern people are living under great stress and continuously increasing workload, and under the effects of known risk factors such as smoking and bad dietary habit etc., it may gradually cause damage to heart and blood vessels. The sudden death from overwork, which is sometimes reported in news, may be due to acute blood vessel injury induced by excessive stress. For these reasons, "stress management" has become an important issue for modern people. Under cumulative long-term stress, the body may release an overdose of steroid and adrenaline that may hurt autonomic nervous system (ANS) and cause imbalance between the parasympathetic and sympathetic contribution in the autonomic nervous system. Symptoms referred to as "autonomic nervous disorder" in medicine may develop, such as dizziness, chest tightness, palpitation, headache, dysphoria, excessive nervousness and anxiety, etc.

Autonomic nervous disorder, which is commonly known as "suboptimal health status", is used to describe symptoms that are hard to explain with physiologic reasons. The suboptimal health status (SHS) is a dynamic status characterized by physiology or psychology in an unobvious stage between health and disease. SHS may develop into a disease for the patient if it is ignored. Alternatively, the patient may recover to well-being if SHS is improved over time. Actually, SHS has direct correlation with what is starting from psychology or physiology stress, and American psychological association has reported that pressure is a silent killer for health.

A measurement method of heart rate variability (HRV) in clinical application started in 1965. The European Society of Cardiology and North American Society of Pacing and Electrophysiology formally published an international standard of "measurement, physiology means and clinical application of "heart rate variability". HRV measurement is non-invasive, quick and convenient etc., so it currently becomes a common method for evaluating whether the function of autonomic nerve is normal. Furthermore, this measurement method is also widely applied for evaluating the psychologic or physiologic stress. When the person is suffering from high stress over a long period of time, the activity of the person's sympathetic nerve is increased and the activity of parasympathetic nerve is decreased, which may cause a physiological response such as increased heartbeat, increased blood pressure, etc. The HRV measurement may show that the low frequency (LF) energy corresponding to the activity of sympathetic nerve may increase, the high frequency (HF) energy corresponding to the activity of parasympathetic nerve may decrease, and LF/HF ratio corresponding to the balance of autonomic nerve may increase. Hence, the LF/HF ratio has been applied widely as a reference index for evaluating the level of stress and has been proved to have a reliable practicability by clinical research. However, in order to calculate the LF/HF ratio based on frequency spectrum statistics formula and the signal of electrocardiogram, complex calculation and high hardware cost are required, which may be disadvantages.

Furthermore, the research article "SDNN/RMSSD as a Surrogate for LF/HF: A Revised Investigation", published in Modelling and Simulation in Engineering by Hui-Min Wang et al in 2012, indicates that a ratio of the standard deviation of all normal to normal intervals (SDNN) and root mean square of the successive differences (RMSSD) calculated based on statistic of the signal of electrocardiogram is roughly similar to LF/HF ratio. For this reason, the SDNN/RMSSD ratio may be used as a reference to indicate whether the function of the autonomic nervous is in balance.

However, the HRV measurement instruments are only used in medical institutions, so it is hard for a general person to often manage the stress state by the HRV measurement in hospital. Currently, electronic blood pressure monitors become essential medical equipment in common families, but architecture of conventional electronic blood pressure monitor or the computing power of a micro-processor of the conventional electronic blood pressure monitor are unable to carry out the complicated calculation of LF/HF ratio. For this reason, the conventional electronic blood pressure monitor is unable to calculate the LF/HF ratio corresponding to the balance of autonomic nerve. In other words, conventional electronic blood pressure monitor is unable to provide the measurement of psychology stress index.

According to the research article "Pulse rate and its correlation with heart rate" published in Journal of Medical and Biological Engineering, vol. 29, pp. 132 by Ming Chang et al in 2009, it had proved that the pulse rate has high correlation with the heart rate. Other research also sequentially reported that the analysis of the waveform of artery blood pressure may be used as a measurement method for evaluating the function of the autonomic nerve, such that the evaluation and management of stress level may become an application of life to make the most use of preventive healthcare.

For this reason, while the blood pressure monitor is measuring the pulse signal of an arm (wrist), it is bound to obtain a convenient reference of stress management of general people if the pulse rate of the pulse signal may be captured for a short period and the pulse rate is then analyzed to quantify the psychology stress index (PSI), and thus the additional value of blood pressure monitor may also be improved.

SUMMARY OF THE PRESENT INVENTION

An objective of the present invention is to define the psychology stress index (PSI) as the SDNN/RMSSD ratio for quantifying the degree of psychology stress, so that the psychology stress index may be measured by a blood pressure measurement device.

Another objective of the present invention is to implement the measure device and method without using a slow speed exhaust valve, so that the architecture of the blood pressure measurement device may be simplified, and the blood pressure measurement device may be used to measure the psychology stress index and blood pressure by means of controlling the pressurization in a variable speed.

In order to achieve the above objectives of the present invention, the present invention provides a measurement device for measuring psychology stress index and blood pressure. The measurement device comprises a micro-processor unit, a display output unit, a button input unit, a pressurizing motor unit, a pressure sensing unit, an airbag unit, and a quick exhaust valve unit. The micro-processor unit is entered into a psychology stress measurement mode according to an operation of the button input unit, wherein while the micro-processor unit controls the pressurizing motor to pressurize the airbag unit with a variable speed, the micro-processor unit measures a pressure signal of the pressure sensing unit, and that when the pressure signal is determined as a pulse signal, the micro-processor unit controls the pressurizing motor unit to stop pressurizing and measures the pulse signal to calculate a psychology stress index and the display output unit outputs the psychology stress index. And, the micro-processor unit is entered into a blood pressure measurement mode according to the operation of the button input unit. While the micro-processor unit controls the pressurizing motor unit to pressurize the airbag unit with a variable speed and after the pressure sensing unit measures a maximum pulse amplitude of the pulse signal, the micro-processor unit controls the pressurizing motor unit to continuously pressurize until the pulse amplitude of the pulse signal is dropped to lower than a pressurization stop amplitude. Then, the micro-processor unit controls the pressurizing motor unit to stop pressurizing and calculates a measurement result according to an amplitude array of the pulse signal and a corresponding pressure array. The display output unit outputs the measurement result.

Preferably, the micro-processor unit controls the pressurizing motor unit to perform a slow speed linear pressurization in the same manner that, while the micro-processor unit controls the pressurizing motor unit to pressurize in the psychology stress index measurement mode or the blood pressure measurement mode, the micro-processor unit controls the pressurizing motor unit to stop pressurizing according to different conditions. In the psychology stress index measurement mode, the micro-processor unit captures interval data of the pulse signal within a period of time after the pressurizing motor unit stops pressurizing, calculates a standard deviation of all normal to normal intervals (SDNN) and a root mean square of the successive differences (RMSSD) according to the interval data, and determines a ratio of SDNN and RMSSD to be the psychology stress index.

In order to achieve the above objectives, the present invention provides a measurement method for measuring psychology stress index and blood pressure, which is applied to a measurement device comprising a micro-processor unit, a display output unit, a button input unit, a pressurizing motor unit, a pressure sensing unit, an airbag unit, and a quick exhaust valve unit. The measurement method includes the following steps:

entering into the psychology stress index measurement mode according to an operation of the button input unit;

measuring a pressure signal of the pressure sensing unit while the micro-processor unit controls the pressurizing motor unit to pressurize the airbag unit with a variable speed;

controlling the pressurizing motor unit to stop pressurizing the airbag unit while the pressure signal is determined as a pulse signal;

measuring the pulse signal to calculate a psychology stress index; and outputting the psychology stress index on the display output unit.

Preferably, the measurement method of the present invention further includes the following steps:

entering into a blood pressure measurement mode according to an operation of the button input unit;

measuring a maximum pulse amplitude of the pulse signal by the pressure sensing unit while the pressurizing motor unit is pressurizing the airbag unit with a variable speed; after the maximum pulse amplitude of the pulse signal is detected;

controlling the pressurizing motor unit to continuously pressurize;

stopping pressurization when the pulse amplitude of the pulse signal is dropped to lower than a pressurization stop amplitude;

obtaining a measurement result according to an amplitude array of the pulse signal and a pressure array corresponding to the amplitude array; and outputting the measurement result on the display output unit.

Preferably, in the measurement method of the present invention, the micro-processor unit controls the pressurizing motor unit to perform a slow speed linear pressurization in the same manner while the micro-processor unit controls the pressurizing motor unit to pressurize in the psychology stress index measurement mode or the blood pressure measurement mode, but the micro-processor unit controls the pressurizing motor unit to stop pressurizing according to different conditions. In the psychology stress index measurement mode, the micro-processor unit captures interval data of the pulse signal within a period of time after the pressurizing motor unit stops pressurizing, calculates a standard deviation of all normal to normal intervals (SDNN) and a root mean square of the successive differences (RMSSD) according to the interval data, and determines a ratio of SDNN and RMSSD to be the psychology stress index.

According to the measurement device and method of the present invention, compared with the calculation of the frequency spectrum indicator (LF/HF), the calculation of the SDNN/RMSSD statistical index is not complicated, so that the hardware cost for the calculation of the SDNN/RMSSD may be dramatically decreased, and the blood pressure measurement device may be able to carry out the measurement of psychology stress index. As a result, common public may have ability to buy and use the measurement device of the present invention.

BRIEF DESCRIPTION OF THE DRAWINGS

The structure, operating principle and effects of the present disclosure will be described in detail by way of various embodiments which are illustrated in the accompanying drawings.

DETAILED DESCRIPTION OF THE PREFERRED EMBODIMENT

The following embodiments of the present invention are herein described in detail with reference to the accompanying drawings. These drawings show specific examples of the embodiments of the present invention. It is to be understood that these embodiments are exemplary implementations and are not to be construed as limiting the scope of the present invention in any way. Further modifications to the disclosed embodiments, as well as other embodiments, are also included within the scope of the appended claims. These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts.

It is to be understood that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present invention. As used herein, the term "or" includes any and all combinations of one or more of the associated listed items.

Figure 1:
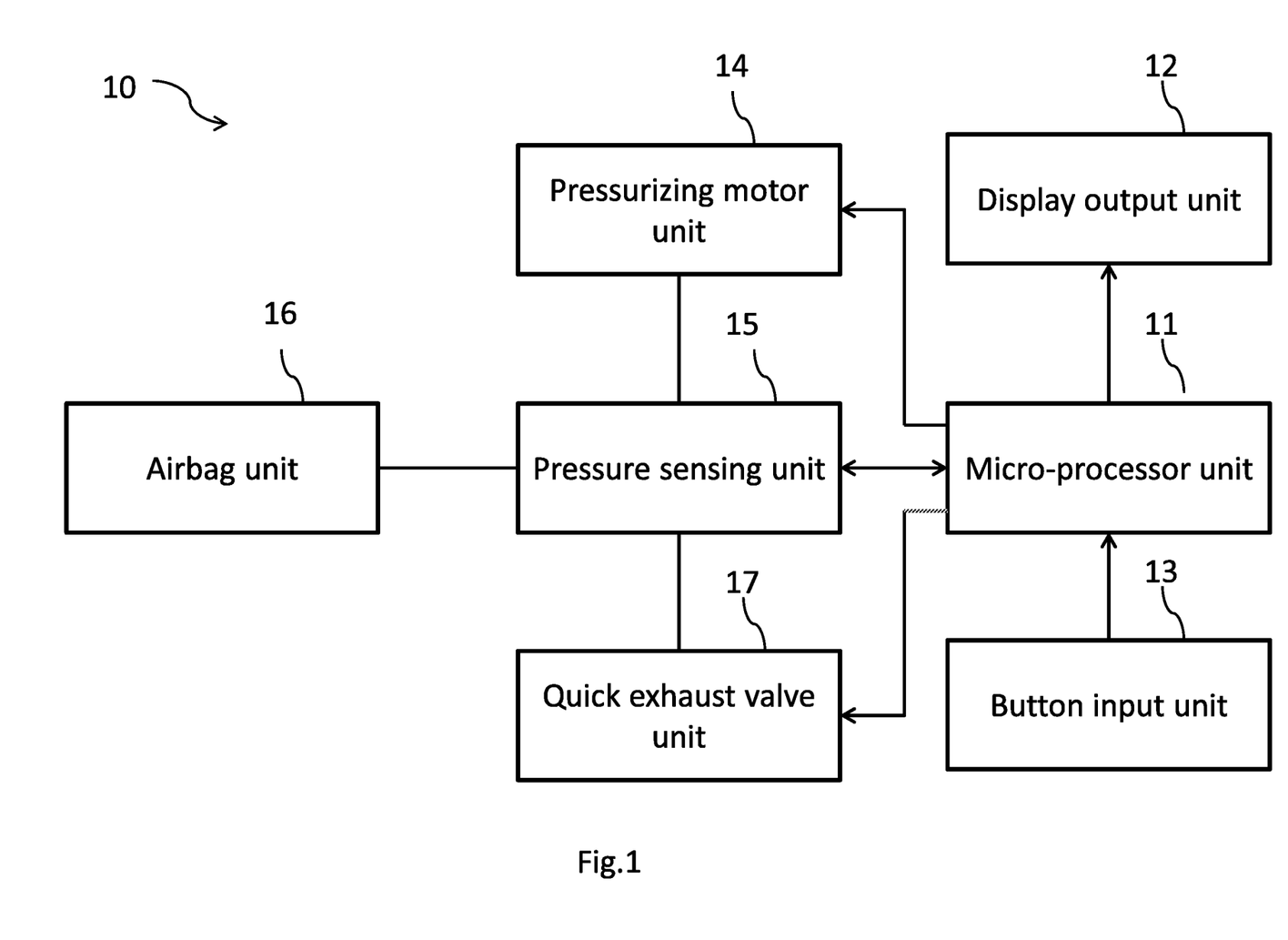
FIG. 1 is a block diagram of a measurement device of the present invention.
Figure 2:
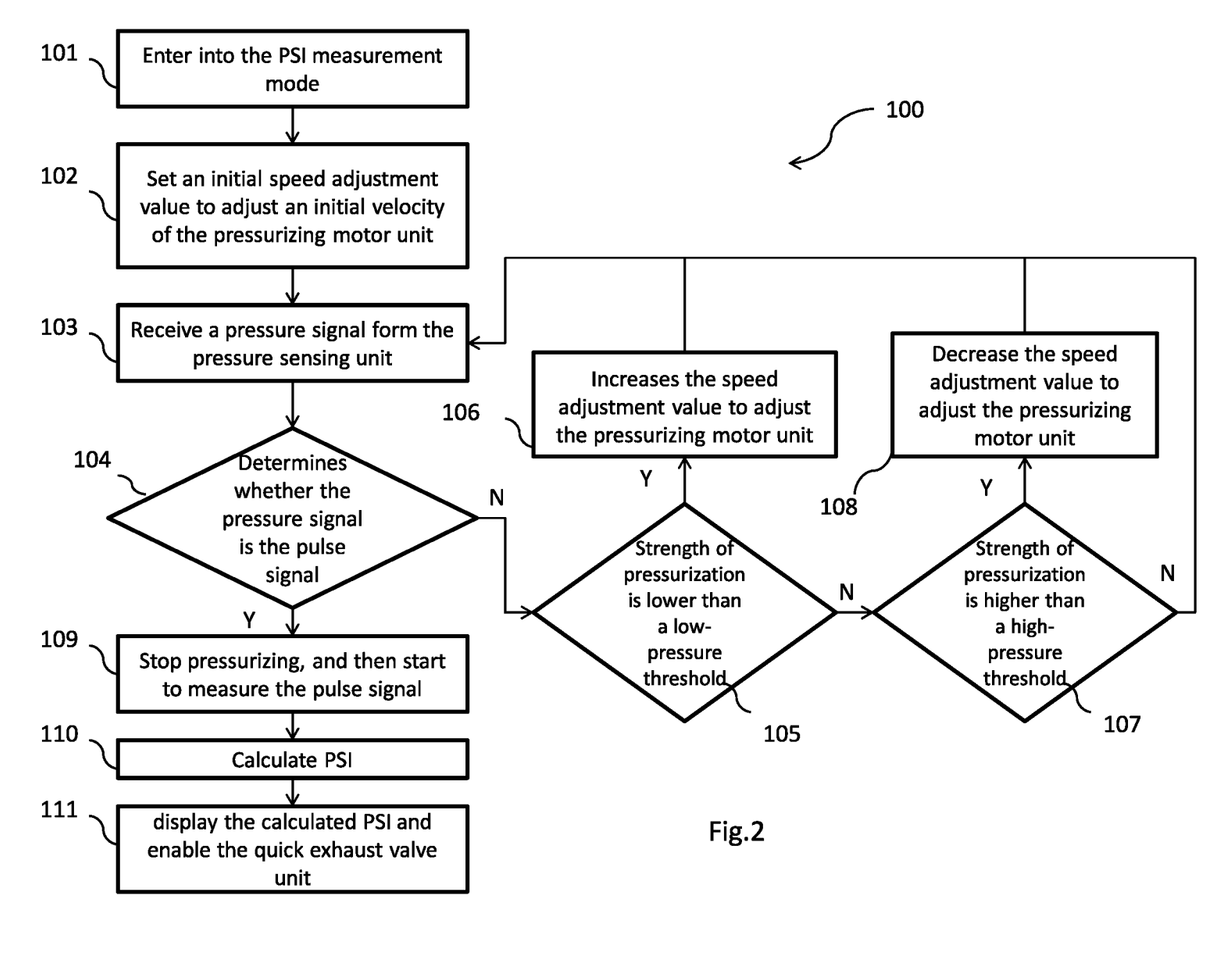
FIG. 2 is a flowchart of a measurement method for measuring a psychology stress index in psychology stress measurement mode, in accordance with the present invention.
Figure 4:
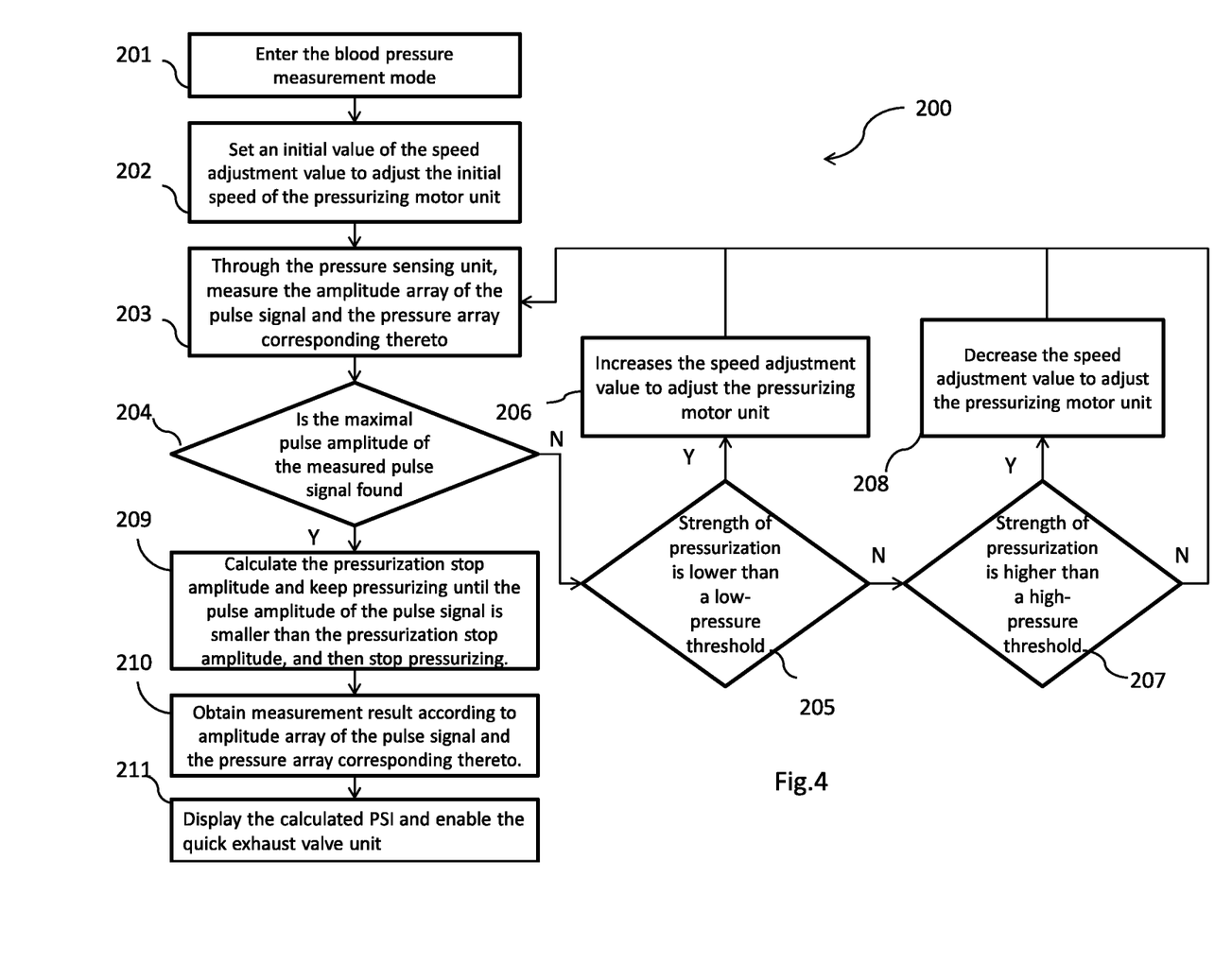
FIG. 4 is a flowchart of the measurement method for measuring blood pressure in blood pressure measurement mode, in accordance with the present invention.

Referring to FIG. 1 of the drawings, a block diagram of the measurement device of the present invention is illustrated. The measurement device 10 of the present invention mainly includes a micro-processor unit 11, a display output unit 12, a button input unit 13, a pressurizing motor unit 14, a pressure sensing unit 15, an airbag unit 16, a quick exhaust valve unit 17, and a power supply unit (not shown in FIG. 1). The power supply unit is configured to provide power to components of measurement device 10 for operation. The airbag unit 16 is an arm sheath airbag unit, and the display output unit 12 is a liquid crystal display (LCD) device. In one embodiment of the present invention, the button input unit 13 includes a function switch button configured to switch the measurement device 10 of the present invention to enter into a psychology stress measurement mode or a blood pressure measurement mode. The micro-processor unit 11 includes a storage unit configured to store a program instruction set, and the micro-processor unit 11 executes the program instruction set to respectively carry out the method for measuring the psychology stress index as illustrated in FIG. 2 in the psychology stress measurement mode or the method for measuring the blood pressure as illustrated in FIG. 4 in the blood pressure measurement mode.

In the measurement device 10 of the present invention, the button input unit 13 is electrically connected to the micro-processor unit 11, and the micro-processor 11 enters into the psychology stress measurement mode according to the operation of the function switch button of the button input unit 13. After entering the psychology stress measurement mode, the micro-processor unit 11 controls, through the pressure sensing unit 15, the pressurizing motor unit 14 to provide variable speed pressurization to the airbag unit 16. The micro-processor unit 11 receives a pressure signal from the pressure sensing unit 15 to determine the pressure situation of the airbag unit 16. While the pressurizing motor unit 14 is being controlled to pressurize with a variable speed, the micro-processor unit 11 analyzes the pressure signal to find a suitable pulse signal. After finding the pulse signal, the micro-processor unit 11 controls the pressurizing motor unit 14 to stop pressurizing, measures the pulse signal to capture time intervals of pulse data, calculates a standard deviation of all normal to normal intervals (SDNN) and a root mean square of the successive differences (RMSSD) according to each of the time intervals, and determines a ratio of SDNN to RMSSD, thereby obtaining the psychology stress index. The display output unit 12 outputs the psychology stress index. After the display output unit 12 displays the psychology stress index, the micro-processor unit 11 controls the quick exhaust valve unit 17 to release the pressure of the airbag unit 16.

In the measurement device 10 of the present invention, the button input unit 13 is electrically connected with the micro-processor unit 11, and the micro-processor unit 11 enters into the blood pressure measurement mode according to operation of the function switch button of button input unit 13. In the blood pressure measurement mode, the micro-processor unit 11 controls the pressurizing motor unit 14, through the pressure sensing unit 15, to pressurize the airbag unit 16 with a variable speed, and the micro-processor unit 11 receives the pressure signal from the pressure sensing unit 15 to determine the pressure situation of the airbag unit 16. While the pressurizing motor unit 14 is being controlled to pressurize with the variable speed, the micro-processor unit 11 measures an amplitude array of the pulse signal sensed by the pressure sensing unit 15 and a pressure array corresponding thereto. After the micro-processor unit 11 determines a maximum pulse amplitude of the pulse signal, the micro-processor unit 11 controls the pressurizing motor unit 14 to continuously pressurize until the pulse amplitude of the pulse signal is dropped to lower than a pressurization stop amplitude X, and then the micro-processor unit 11 controls the pressurizing motor unit 14 to stop pressurizing. Afterwards, according to the amplitude array of the pulse signal and the pressure array corresponding thereto, the micro-processor unit 11 obtains a measurement result including systolic pressure, diastolic pressure and cardiac rate, and so on. The display output unit 12 outputs the measurement result. After the display output unit 12 displays the measurement result, the micro-processor unit 11 controls the quick exhaust valve unit 17 to release pressure of the airbag unit 16.

According to an embodiment of the present disclosure, in the psychology stress measurement mode and the blood pressure measurement mode, the micro-processor unit 11 controls the pressurizing motor unit 14 to perform slow-speed linear pressurization in the same manner, but the micro-processor unit 11 controls the pressurizing motor unit 14 to stop pressurizing according to different conditions. In the psychology stress measurement mode, the micro-processor unit 11 controls the pressurizing motor unit 14 to stop pressurizing when the micro-processor unit 11 determines the pressure signal of pressure sensing unit 15 to be the pulse signal, and then starts to measure and calculate the pulse data of psychology stress. In the blood pressure measurement mode, after the pressure sensing unit 11 detects the maximum pulse amplitude of the pressure signal, the micro-processor unit 11 controls the pressurizing motor unit 14 to continuously pressurize until the pulse amplitude of the pressure signal is dropped to lower than the pressurization stop amplitude X, and the micro-processor unit 11 then controls the pressurizing motor unit 14 to stop pressurizing, and then obtains the measurement result including systolic pressure, diastolic pressure and cardiac rate and so on. according to the amplitude array of pulse signal and the pressure array corresponding thereto measured within a period of the variable speed pressurization. The manner that the micro-processor unit 11 controls the pressurizing motor unit 14 to perform variable speed pressurization within the period of variable speed pressurization will be described as follow.

Referring to FIG. 2 of the drawings, a flowchart of the measurement method of measuring the psychology stress index in psychology stress measurement mode is illustrated in accordance with the present disclosure. In one embodiment of the present invention, the micro-processor unit 11 executes the program instruction set stored in storage unit to carry out the method 100 for measuring the psychology stress index of the present disclosure. In a step 101, the micro-processor unit 11 enters into the psychology stress index (PSI) measurement mode according to the operation of the function switch button of the button input unit 13. In a step 102, the micro-processor unit 11 sets an initial speed adjustment value and adjusts an initial velocity of the pressurizing motor unit 14 according to the speed adjustment value to pressurize to the airbag unit 16. During the variable-speed pressurization, the micro-processor unit 11 adjusts the speed adjustment value according to a high pressure threshold and a low pressure threshold. For example, the micro-processor unit may control a pressurized rate of the pressurizing motor unit according to a high pressure threshold and a low pressure threshold. In a step 103, the micro-processor unit 11 receives a pressure signal from the pressure sensing unit 15 to detect the pressure situation of the airbag unit 16.

In a step 104, the micro-processor unit 11 determines whether the pressure signal is the pulse signal rather than noise, and performs step 109 when the pressure signal is determined to be the pulse signal or performs step 105 when the pressure signal is determined not to be the pulse signal. According to one embodiment of the present invention, while the pressurizing motor unit 14 is pressurizing the airbag unit 16, the micro-processor unit 11 calculates data of the wave crest and wave trough of the pulse signal according to the pressure signal of the pressure sensing unit 15. In one embodiment of the present invention, three characteristics of the data of the wave crest and wave trough of the pulse signal are used to determine that the pulse signal is heartbeat rather than noise. The first characteristic is the characteristic of the wave crest, wherein eight sample points are captured to find the wave crest, the top of the wave is the highest value of the eight sample points, and the points at the two sides of the top are lowering points. The second characteristic is wave trough characteristic, wherein eight sample points are captured to find the wave trough, the bottom of wave is the lowest value of the eight sample points, and the points at the two sides of the bottom are rising points. The third characteristic is amplitude size, wherein difference of the wave crest and the wave trough must be higher than an experience value of the amplitude of a heartbeat. The experience value may be obtained by one skilled in the art according to the clinical statistics. According to aforementioned three characteristics, the micro-processor unit 11 may determine the pressure signal to be the pulse signal rather than noise.

Steps 105-108 are for the variable-speed pressurization manner of the pressurizing motor unit 14 which is controlled by the micro-processor unit 11 in the psychology stress index (PSI) measurement mode. In the step 105, through pressure sensing unit 15, the micro-processor unit 11 determines whether the strength of pressurization of the pressurizing motor unit 14 is lower than a low-pressure threshold, and then performs the step 106 when the strength is lower than a low-pressure threshold, or performs the step 107 when the strength is higher than a low-pressure threshold. In the step 106, the micro-processor unit 11 increases the speed adjustment value to adjust the pressurizing motor unit 14, and then performs the step 103. In the step 107, the micro-processor unit 11 determines whether the strength of the pressurization is higher than a high-pressure threshold (for example, a pressure value of the pressure signal is higher than the high-pressure threshold), and performs a step 108 when the strength is higher than a high-pressure threshold or performs the step 103 when the strength is lower than the high pressure threshold. In the step 108, the micro-processor unit 11 decreases the speed adjustment value to adjust the pressurizing motor unit 14, and then performs the step 103. According to one embodiment of the present invention, the low-pressure threshold and high-pressure threshold may be respectively set as 2 mmHg and 6 mmHg. Such controlled manner may satisfy the requirement for slow-speed linear pressurization, so that the measurement device of the present invention may be implemented without using a slow speed exhaust valve. In addition, by using the technology of pressurization as well as detection, the method of the present invention may measure the PSI without the circuit required for electrocardiogram, and the complicated calculation for PSI may be reduced.

Figure 3:
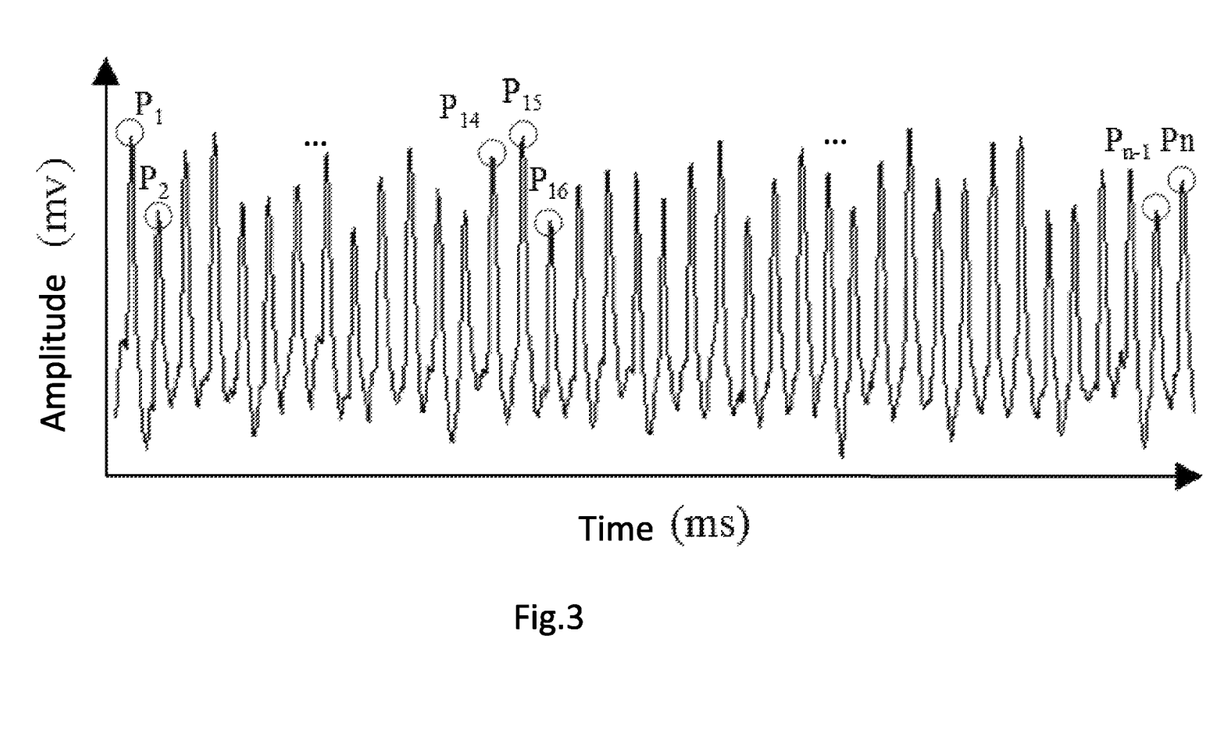
FIG. 3 is a waveform diagram of a pulse signal within a period after pressurization is stopped in the psychology stress measurement mode of the present invention.

In a step 109, the micro-processor unit 11 controls the pressurizing motor unit 14 to stop pressurizing after the micro-processor unit 11 determines the pressure signal to be the pulse signal rather than noise, and then starts to measure the pulse signal. The pulse signal is measured in a manner of capturing a plurality of wave crest values P1, P2, . . . , Pn of the pulse signal within a time interval, as shown in the waveform diagram of the pulse signal of FIG. 3. In a step 110, the micro-processor unit 11 may calculate a sequence of peak to peak intervals {PP1, PP2, PP3, . . . , PPn}, (that is, PP1=P2−P1, PP2=P3−P2, . . . , and so on), and calculate a mean value of the peak to peak intervals ( ). The micro-processor unit 11 then calculates and obtains the standard deviation of all normal to normal intervals (SDNN) and root mean square of the successive differences (RMSSD) according to the following formulas:

The micro-processor unit 11 calculates the ratio of SDNN to RMSSD. The ratio is used as the psychology stress index.

In a step 111, the micro-processor unit 11 displays the calculated PSI on display output unit 12, and controls the quick exhaust valve unit 17 to release the pressure of the airbag unit 16.

Figure 5:
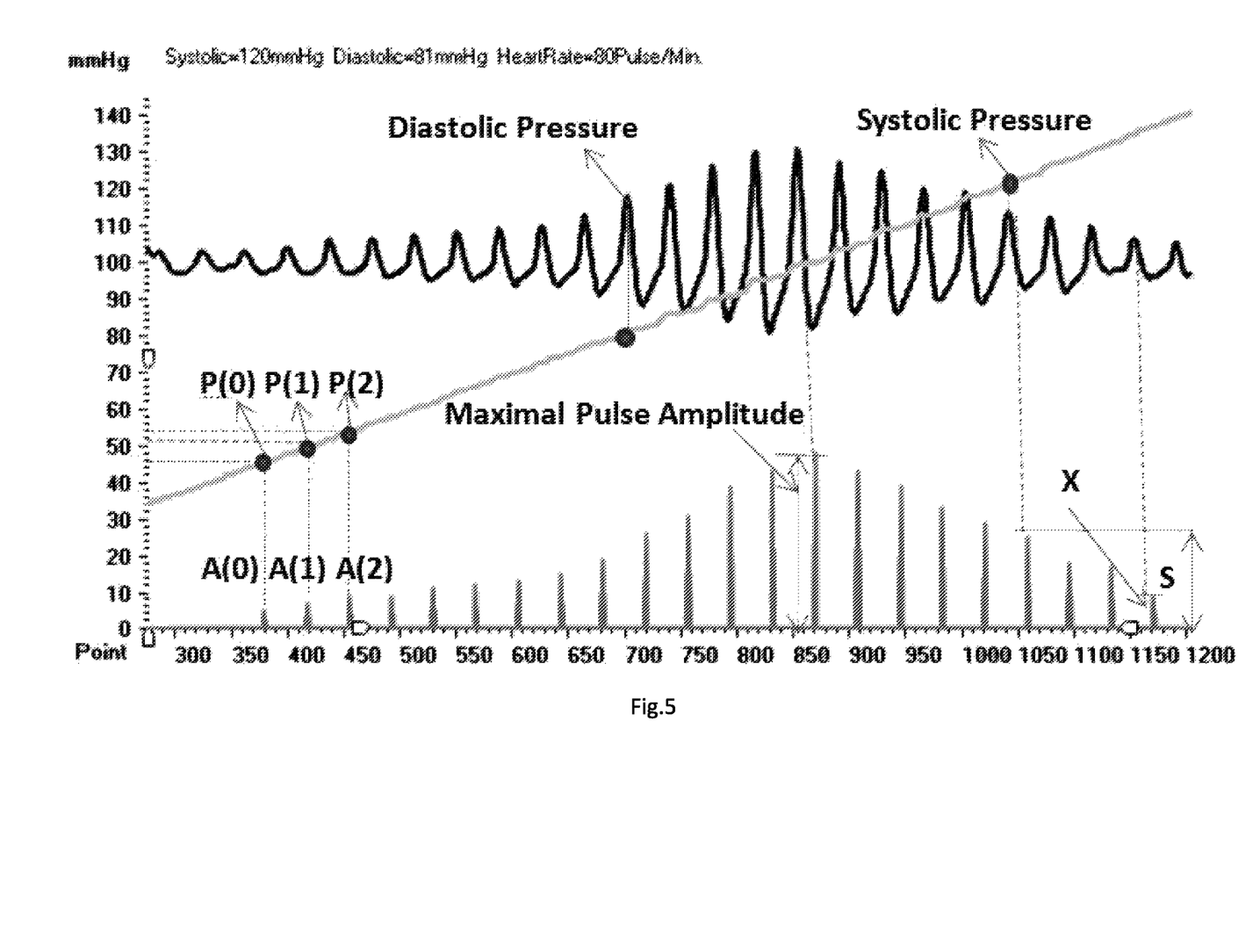
FIG. 5 is a waveform diagram of pulse signal within a period of variable-speed pressurization in blood pressure measurement mode, in accordance with the present invention.

Referring to FIG. 4 of the drawings, a flowchart showing the steps in an operation of the method for measuring the blood pressure in the blood pressure measurement mode is illustrated, in accordance with the present invention. In one embodiment of the present invention, the micro-processor unit 11 executes the program instruction set stored in the storage unit, in order to perform the method 200 of the present invention for measuring the blood pressure. In a step 201, the micro-processor unit 11 enters the blood pressure measurement mode according to the operation of the function switch button of the button input unit 13. In a step 202, the micro-processor unit 11 sets an initial value of the speed adjustment value, and adjust the initial speed of the pressurizing motor unit 14 according to the speed adjustment value, so that the pressurizing motor unit 14 may perform pressurization on the airbag unit 16. During the variable speed pressurization, the micro-processor unit 11 adjusts the speed adjustment value according to the high-pressure threshold and the low-pressure threshold. In a step 203, through the pressure sensing unit, the micro-processor unit 11 measures the pulse signal and records the amplitude array A(0), A(1), . . . of the pulse signal and the pressure array P(0), P(1), . . . corresponding thereto, as shown in FIG. 5.

In a step 204, the micro-processor unit 11 determines whether the maximal pulse amplitude of the measured pulse signal is found, and that when determining the maximal pulse amplitude is found, the micro-processor unit 11 performs a step 209, and when determining the maximal pulse amplitude is not found, the micro-processor unit 11 performs the step 205. In one embodiment of the present invention, when the micro-processor unit 11 finds the maximum value in the amplitude array A(0), A(1), . . . of the pulse signal, it indicates that the micro-processor unit 11 finds the maximal pulse amplitude of the pulse signal.

The steps 205-208 describe the manner that the micro-processor unit 11 controls the pressurizing motor unit 14 to perform variable speed pressurization in the blood pressure measurement mode, wherein this manner is the same as that in PSI measurement mode, such as the descriptions of the steps 105-108 shown in FIG. 2. By performing steps 205-208, the slow speed linear pressurization as shown in FIG. 5 may be achieved, so that the measurement device of the present invention may be implemented without using the slow speed exhaust valve.

In a step 209, after the micro-processor unit 11 measures the maximal pulse amplitude of the pulse signal, the micro-processor unit 11 calculates the pressurization stop amplitude X. In one embodiment of the present invention, the formula for calculating the pressurization atop amplitude X is, wherein S is a threshold for finding the systolic pressure, and C is a constant value smaller than 1. The value of S may be obtained by one skilled in the art according to the clinical statistics. In order to prevent the threshold misjudgment of the systolic pressure, the pressurization stop amplitude X may be set to be lower than the threshold S, thereby ensuring accuracy of the measurement data. In the step 209, while calculating the pressurization stop amplitude X, the micro-processor unit 11 also controls the pressurizing motor unit 14 to continuously perform slow speed linear pressurization until the pulse amplitude of the pulse signal is smaller than the pressurization stop amplitude X, and that after the pulse amplitude of the pulse signal is smaller than the pressurization stop amplitude X, the micro-processor unit 11 controls the pressurizing motor unit 14 to stop pressurizing, and the micro-processor unit 11 then performs a step 210.

In the step 210, as shown in FIG. 5, the micro-processor unit 11 calculates the systolic pressure and the diastolic pressure of the blood pressure and heart-rate according to the amplitude array A(0), A(1), . . . of the pulse signal recorded during the variable speed pressurization, and the pressure array P(0), P(1), . . . corresponding to the amplitude array, in order to obtain the measurement result. One of ordinary skill in the art is able to effortlessly achieve the step 210. In a step 211, the micro-processor unit 11 displays the measurement result, including the systolic pressure, the diastolic pressure and heart-rate and so on, on the display output unit 12, and controls the quick exhaust valve unit 17 to release the pressure of the airbag unit 16.

Figure 6:
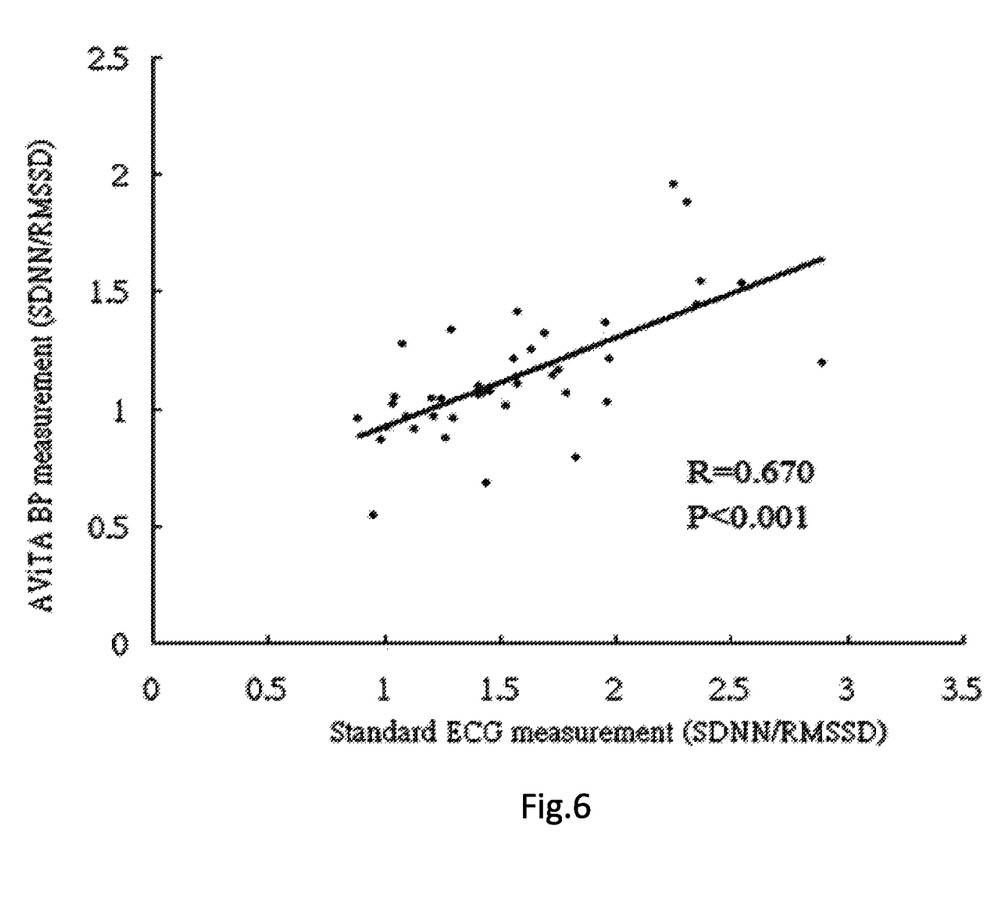
FIG. 6 is a diagram showing correlation between the psychology stress index measured by measurement method of the present invention and the stress state according to analyzing HRV by traditional ECG.

Referring to FIG. 6 of the drawings, a diagram shows correlation between the psychology stress index measured by method of the present disclosure and the stress state according to analyzing HRV by traditional ECG is illustrated. The key point of FIG. 6 is to validate the correlation between two measurement instruments, to make sure that the psychology stress index analyzed based on the blood pressure pulse of the present invention has high correlation with HRV measurement analyzed by traditional ECG. ECG_HRV instrument (Unisage) used in the clinic is operated to perform the correlation analysis, wherein 40 people are measured as samples to obtain measurement data. Compared to measurement results of the standard instrument and the measurement device of the present invention, it may be found that the result data of electrocardiogram has significant medium-high correlation with the psychology stress index parameter of the present invention in statistics. As a result, the psychology stress index of the present invention and the psychology stress index of standard instrument are correlated.

The present invention disclosed herein has been described by means of specific embodiments. However, numerous modifications, variations and enhancements can be made thereto by those skilled in the art without departing from the spirit and scope of the invention set forth in the claims.

What is claimed is:

1. A measurement device for measuring psychology stress index and blood pressure, comprising:
   a display output unit,
   a button input unit,
   a pressurizing motor unit,
   one pressure sensing unit,
   one airbag unit,
   a quick exhaust valve unit, and
   a micro-processor unit which is selectively entered into one of a psychology stress measurement mode and a blood pressure measurement mode according to an operation of the button input unit, wherein while the micro-processor unit controls a pressurized rate of the pressurizing motor unit to pressurize the airbag unit with a slow speed linear pressurization in a same manner that the micro-processor unit controls the pressurizing motor unit to pressurize in the psychology stress index measurement mode and the blood pressure measurement mode, the micro-processor unit controls the pressurizing motor unit to stop pressurizing according to different conditions,
   wherein under the psychology stress measurement mode, the micro-processor unit measures a pressure signal of the pressure sensing unit, wherein during pressurizing the airbag unit with a slow speed linear pressurization, the micro-processor unit calculates the amplitude size between the wave crest and the wave trough, according to the pressure signal, to determine the pressure signal becoming a pulse signal, and the micro-processor unit controls the pressurizing motor unit to stop pressurizing, and then the micro-processor unit measures the pulse signal to calculate a psychology stress index according to a sequence of peak to peak intervals of the pulse signal within a time interval, wherein under the blood pressure measurement mode, after the pressure sensing unit measures a maximum pulse amplitude of the pressure signal, the micro-processor unit controls the pressurizing motor unit to continuously pressurize until the maximum pulse amplitude of the pressure signal is dropped to lower than a pressurization stop amplitude, and the micro-processor unit then controls the pressurizing motor unit to stop pressurizing.

2. The measurement device of claim 1, wherein when the micro-processor unit is in the psychology stress measurement mode and controls the pressurizing motor unit to pressurize the airbag unit with the variable speed, the micro-processor unit controls the pressurized rate of the pressurizing motor unit to maintain a pressure value of the pressure signal between a high pressure threshold and a low pressure threshold.

3. The measurement device of claim 2, wherein the micro-processor unit controls the pressurizing motor unit to decrease the pressurized rate when the pressure value of the pressure signal is higher than the high pressure threshold, and the micro-processor unit controls the pressurizing motor unit to increase the pressurized rate when the pressure value of the pressure signal is lower than the high pressure threshold.

4. The measurement device of claim 2, wherein the high pressure threshold is 6 mm Hg and the low pressure threshold is 2 mm Hg.

5. The measurement device of claim 1, wherein the micro-processor unit determines whether the pressure signal is the pulse signal, according to characteristics of wave crest, wave trough, amplitude or a combination thereof of the pressure signal.

6. The measurement device of claim 1, wherein the micro-processor unit controls the quick exhaust valve unit to release the pressure of the airbag unit, and the airbag unit is an arm sheath airbag unit.

7. The measurement device of claim 1, wherein the micro-processor unit comprises a storage unit, the storage unit is configured to store a program instruction set, and the micro-processor unit executes the program instruction set to control the pressurizing motor unit.

8. A pressurization control method for measuring psychology stress index and blood pressure, applied to a measurement device comprising a micro-processor unit, a display output unit, a button input unit, a pressurizing motor unit, one pressure sensing unit, one airbag unit and a quick exhaust valve unit, wherein the pressurization control method comprising:

entering into one of a psychology stress index measurement mode and a blood pressure measurement mode according to an operation of the button input unit; and under the one of the psychology stress index measurement mode and the blood pressure measurement mode, controlling a pressurized rate of the pressurizing motor unit to pressurize the airbag unit with a slow speed linear pressurization in a same manner that the micro-processor unit controls the pressurizing motor unit to pressurize in one of the psychology stress index measurement mode and the blood pressure measurement mode, while the micro-processor unit controls the pressurizing motor unit to stop pressurizing according to different conditions, wherein under the psychology stress measurement mode, the micro-processor unit measures a pressure signal of the pressure sensing unit, and during pressurizing the airbag unit with a slow speed linear pressurization, the micro-processor unit calculates the amplitude size between the wave crest and the wave trough, according to the pressure signal, to determine the pressure signal becoming a pulse signal, and the micro-processor unit controls the pressurizing motor unit to stop pressurizing, and then the micro-processor unit measures the pulse signal to calculate a psychology stress index according to a sequence of peak to peak intervals of the pulse signal within a time interval, wherein under the blood pressure measurement mode, after the pressure sensing unit measures a maximum pulse amplitude of the pressure signal, the micro-processor unit controls the pressurizing motor unit to continuously pressurize until the maximum pulse amplitude of the pressure signal is dropped to lower than a pressurization stop amplitude, and the micro-processor unit then controls the pressurizing motor unit to stop pressurizing.

9. The pressurization control method of claim 8, further comprising:

controlling the pressurizing motor unit, by the micro-processor unit, to pressurize the airbag unit with a slow speed linear pressurization, to maintain a pressure value of the pressure signal between a high pressure threshold and a low pressure threshold.

* * * * *